(12) United States Patent
Cherubini et al.

(10) Patent No.: US 9,957,111 B2
(45) Date of Patent: May 1, 2018

(54) LABORATORY DISTRIBUTION SYSTEM FOR CONVEYING TEST TUBE HOLDERS

(71) Applicant: Roche Diagnostics Operations, Inc., Indianapolis, IN (US)

(72) Inventors: Claudio Cherubini, Cham (CH); Andreas Drechsler, Baar (CH); Reto Huesser, Cham (CH); Nenad Milicevic, Baar (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days. days.

(21) Appl. No.: 15/276,148

(22) Filed: Sep. 26, 2016

(65) Prior Publication Data

US 2017/0101272 A1    Apr. 13, 2017

(30) Foreign Application Priority Data

Oct. 7, 2015 (EP) .................................. 15188806

(51) Int. Cl.
*B65G 33/04* (2006.01)
*B65G 33/06* (2006.01)

(52) U.S. Cl.
CPC ............. *B65G 33/04* (2013.01); *B65G 33/06* (2013.01)

(58) Field of Classification Search
CPC ................................ B65G 33/04; B65G 33/06
See application file for complete search history.

(56) References Cited

U.S. PATENT DOCUMENTS

| | | | | |
|---|---|---|---|---|
| 1,892,206 A | | 12/1932 | Dietz | |
| 2,417,823 A | * | 3/1947 | Hodson | B65G 33/06 198/467.1 |
| 2,628,708 A | * | 2/1953 | Wahl | B65G 11/203 198/724 |
| 3,036,624 A | * | 5/1962 | Carter | B65B 35/26 156/566 |
| 5,297,668 A | * | 3/1994 | Zink | B65G 21/18 198/724 |
| 5,699,891 A | | 12/1997 | Gosdowski et al. | |

(Continued)

FOREIGN PATENT DOCUMENTS

| | | |
|---|---|---|
| CN | 201133910 Y | 10/2008 |
| CN | 204613223 U | 9/2015 |

(Continued)

*Primary Examiner* — Thomas Randazzo
(74) *Attorney, Agent, or Firm* — Roche Diagnostics Operations, Inc.

(57) ABSTRACT

A conveyor device for conveying test tube holders in a laboratory distribution system is presented. The conveyor device is a screw conveyor device comprising a helical track having a helix axis and a drive shaft having an axis of rotation parallel or coaxial to the helix axis, which drive shaft is adapted to be driven to rotate about the axis of rotation for causing a movement of one test tube holder or a plurality of test tube holders contacting the helical track between an entry region and an exit region. The entry region and the exit region are spaced in a direction of the helix axis. A laboratory distribution system for conveying test tube holders and a laboratory automation system comprising a laboratory distribution system are also presented.

15 Claims, 4 Drawing Sheets

(56) References Cited

U.S. PATENT DOCUMENTS

| | | | |
|---|---|---|---|
| 5,765,675 A * | 6/1998 | Draghetti | B65G 33/04 131/94 |
| 5,800,780 A | 9/1998 | Markin | |
| 6,053,303 A * | 4/2000 | Wang | B65G 33/04 198/778 |
| 6,056,106 A | 5/2000 | van Dyke, Jr. et al. | |
| 6,520,313 B1 | 2/2003 | Kaarakainen et al. | |
| 7,152,504 B2 | 12/2006 | Itoh | |
| 8,877,128 B2 | 11/2014 | Fukugaki et al. | |
| 2006/0245865 A1 | 11/2006 | Babson | |
| 2013/0233673 A1* | 9/2013 | Itoh | B65G 33/06 198/467.1 |
| 2013/0239527 A1 | 9/2013 | Clarke et al. | |
| 2014/0342465 A1 | 11/2014 | Haechler et al. | |
| 2015/0177268 A1 | 6/2015 | Reisch et al. | |
| 2015/0233955 A1 | 8/2015 | Nemoto et al. | |
| 2017/0212139 A1 | 7/2017 | Jaeggi | |
| 2017/0212140 A1 | 7/2017 | Ferihumer et al. | |
| 2017/0212141 A1 | 7/2017 | Schacher et al. | |

FOREIGN PATENT DOCUMENTS

| | | |
|---|---|---|
| EP | 2485058 A1 | 8/2012 |
| EP | 2253960 B1 | 5/2013 |
| EP | 2887071 A1 | 6/2015 |
| GB | 797685 | 7/1958 |
| JP | H07-234228 A | 9/1995 |
| JP | 2004-223646 A | 8/2004 |
| JP | 2014-147877 A1 | 9/2014 |
| WO | 1983/000393 A1 | 2/1983 |
| WO | 2011/138448 A1 | 11/2011 |
| WO | 2015/059620 A1 | 4/2015 |

\* cited by examiner

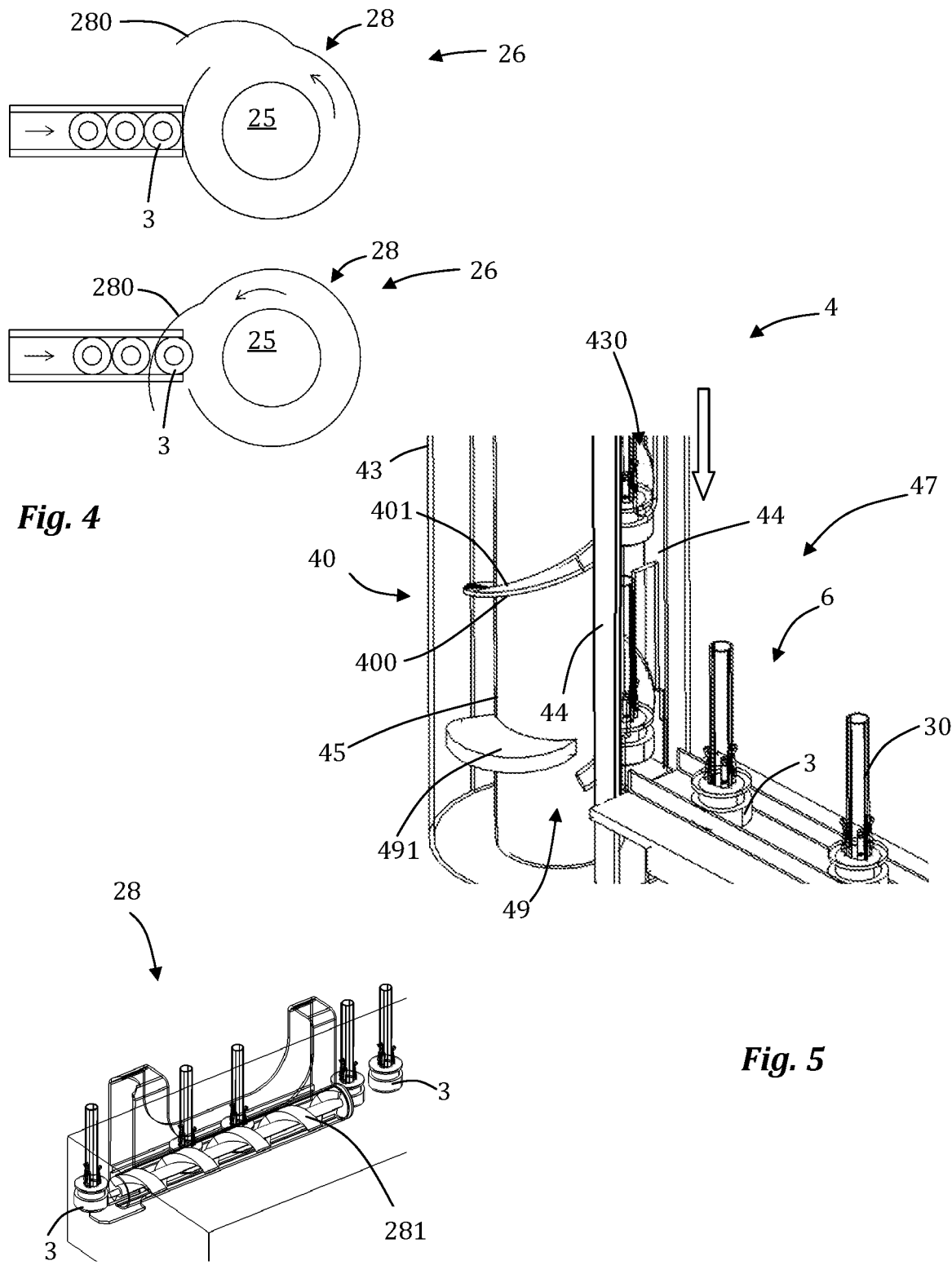

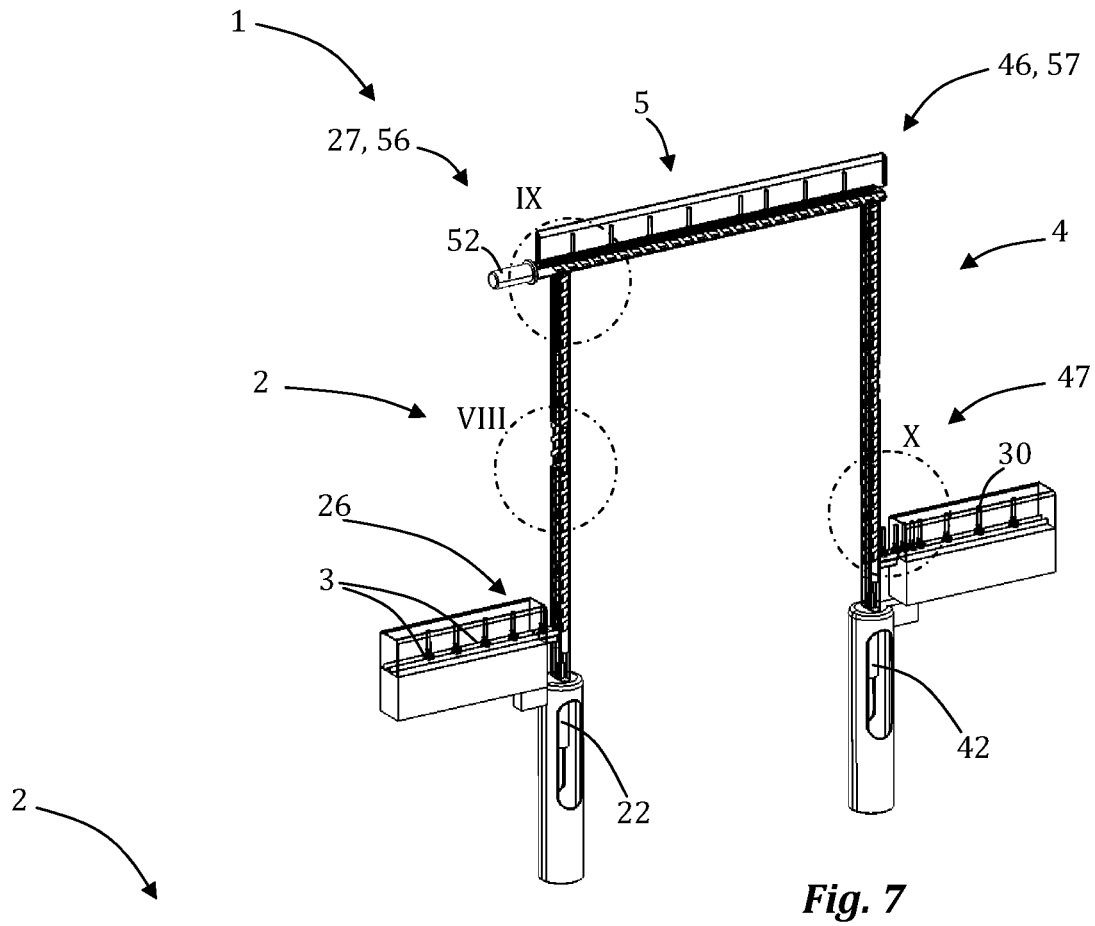
*Fig. 7*
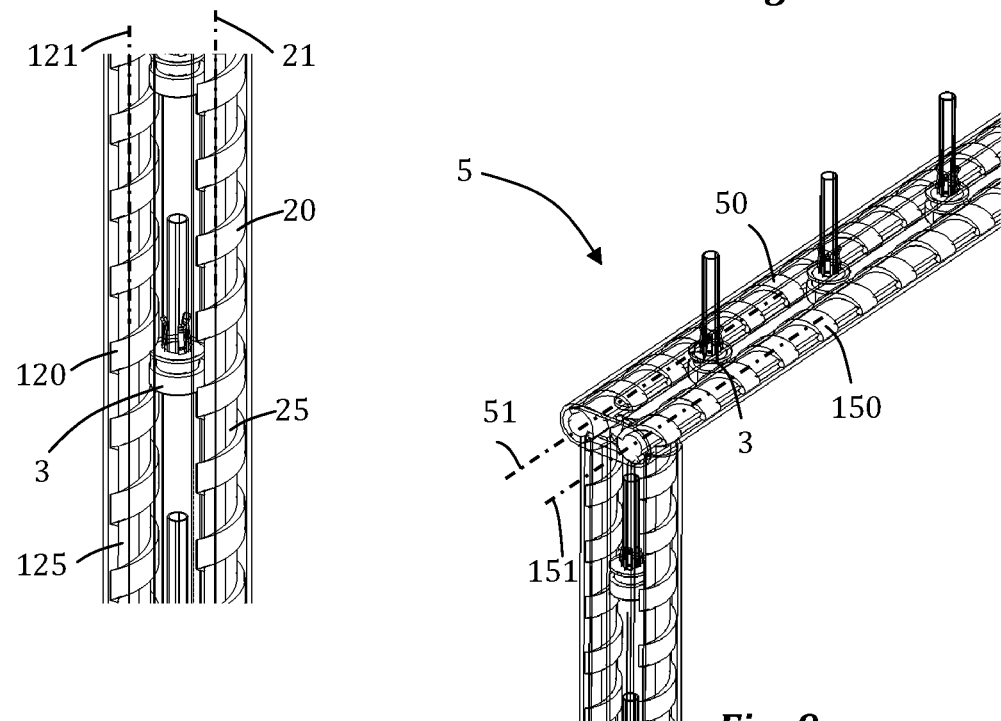
*Fig. 8*
*Fig. 9*

LABORATORY DISTRIBUTION SYSTEM FOR CONVEYING TEST TUBE HOLDERS

CROSS-REFERENCE TO RELATED APPLICATIONS

This application claims priority to EP 15188806.2, filed Oct. 7, 2015, which is hereby incorporated by reference.

BACKGROUND

The present disclosure relates to a conveyor device for conveying test tube holders in a laboratory distribution system a laboratory distribution system for conveying test tube holders and to a laboratory automation system comprising a laboratory distribution system.

A laboratory automation system comprises a number of pre-analytical, analytical and/or post-analytical stations, in which samples, for example blood, saliva, swab and other specimens taken from the human body, are processed. It is generally known to provide test tubes containing the samples. The test tubes are also referred to as sample tubes.

For an individual distribution of the test tubes to designated stations or modules of the laboratory automation system, it is known to provide test tube holders, also referred to as single test tube holders, test tube carriers or pucks, having a retaining area for retaining a single test tube in a vertical orientation. The test tubes are either capped or uncapped depending on the intended processing or stage of the processing. By the distribution system, test tube holders retaining test tubes as well as empty test tube holders are moved between the various stations. If possible measures are taken to ensure that the test tubes are only routed to designated stations or modules in order to achieve minimal turnaround times.

For minimizing a space requirement of the laboratory automation system, it is known to provide stations at different levels. Further, laboratory automation systems are known, wherein analytical stations are provided in different rooms on various floors. Such laboratory automation systems require a conveyor for lifting or lowering the test tube holders between different levels. In addition, it is known to lift or lower test tube holders in order to provide walkways or passageways crossing the movement path of the test tube holders.

Therefore, there is a need for a reliable conveyor device which can be manufactured in a simple and cost effective manner.

SUMMARY

According to the present disclosure, a conveyor device for conveying test tube holders in a laboratory distribution system is presented. The conveyor device can comprise a screw conveyor device comprising a helical track having a helix axis and a drive shaft having an axis of rotation parallel, or coaxial, to the helix axis. The drive shaft can be adapted to be driven to rotate about the axis of rotation for causing a movement of a test tube holder, or a plurality of test tube holders, contacting the helical track between an entry region and an exit region. The entry region and the exit region can be spaced in a direction of the helix axis.

Accordingly, it is a feature of the embodiments of the present disclosure to provide for a reliable conveyor device which can be manufactured in a simple and cost effective manner. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 4 illustrates a top view of a detail IV showing an entry region of the first vertical screw conveyer device of the laboratory distribution system shown in FIG. 1 according to an embodiment of the present disclosure.

FIG. 5 illustrates a detail V showing an exit region of the second vertical screw conveyer device of the laboratory distribution system shown in FIG. 1 according to an embodiment of the present disclosure.

FIG. 6 illustrates an alternative embodiment of a loading module for the first vertical screw conveyer device of a laboratory distribution system similar to that shown in FIG. 1 according to a second embodiment of the present disclosure.

FIG. 7 illustrates a perspective view a third embodiment of a laboratory distribution system similar to FIG. 1 according to an embodiment of the present disclosure.

FIG. 8 illustrates a detail VIII of FIG. 7 similar to FIG. 2 of the embodiment shown in FIG. 7 according to an embodiment of the present disclosure.

FIG. 9 illustrates a detail IX of a laboratory distribution system shown in FIG. 7 similar to FIG. 3 according to an embodiment of the present disclosure.

DETAILED DESCRIPTION

Figure 1:
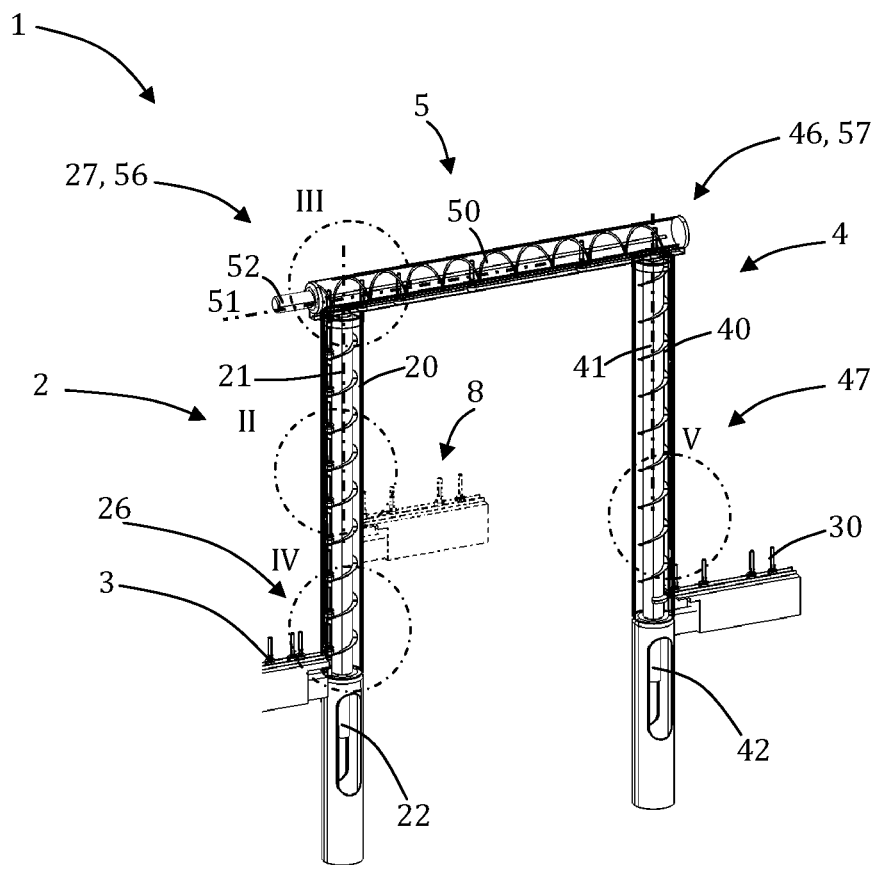
FIG. 1 illustrates a perspective view of a laboratory distribution system comprising a first vertical screw conveyer device for an upward movement of test tube holders, a second vertical screw conveyor device for a downward movement of test tube holders and a horizontal screw conveyer device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A screw conveyor device for conveying test tube holders in a laboratory distribution system is provided. The screw conveyor device can comprise a helical track having a helix axis and a drive shaft having an axis of rotation parallel, or coaxial, to the helix axis. The drive shaft can be adapted to be driven to rotate about the axis of rotation for causing a movement of one test tube holder, or a plurality of test tube holders, contacting the helical track between an entry region and an exit region. The entry region and the exit region can be spaced in a direction of the helix axis.

The one test tube holder, or the plurality of test tube holders, can be conveyed either empty or while retaining a test tube. The screw conveyor device can allow for a smooth and jolt-free movement of the test tube holder(s) relative to the helical track. Therefore, test tube holders retaining capped or uncapped test tube can be moved by the screw conveyor device.

The screw conveyor device can be used for a horizontal, as well as for a vertical, movement of test tube holders. In one embodiment, the screw conveyor device can be a vertical screw conveyor device having a vertical helix axis.

The screw conveyor device can be of different design. A rotation of the drive shaft can cause a relative rotation of the helical track and at least one test tube holder conveyed by the screw conveyor device about the helix axis resulting in a movement of the test tube holders in parallel to the helix axis, for example if the screw conveyor device is a vertical screw conveyor device an upward or downward movement of the test tube holders.

In one embodiment, the helical track can be coupled to the drive shaft to rotate about the helix axis. In one embodiment, a shaftless helical track can be provided, which can be coupled at one end to the drive shaft. The shaftless helical track, in one embodiment, can cooperate with a stationary central core element having a guide for guiding the test tube holders to move in parallel to the helix axis. Alternatively, or in addition, a tubular housing surrounding the helical track can be provided with a guide for guiding the test tube holders to move in parallel to the helix axis. In one embodiment, the central core element and/or the tubular housing can be provided with grooves extending in the direction of the helix axis for guiding the test tube holders and preventing a movement of the test tube holders with the helical track.

In some embodiments, the helical track can be provided on a coaxial central shaft in which central shaft driven by the drive shaft to rotate about the helix axis. In one embodiment, the helical track can be provided as a blade protruding in radial direction from the central shaft.

In other embodiments, a groove can be provided at a circumference of the central shaft for forming the helical track. The central shaft, in one embodiment, can be formed integrally with the drive shaft or fixedly mounted to the drive shaft. In other embodiments, the central shaft can be coupled to the drive shaft via a gear system. In order to prevent a test tube holder conveyed by the screw conveyor device from rotating with the helical track, in one embodiment, in the case of a lateral or horizontal screw conveyor having a horizontal helix axis, use can be made of friction and/or gravitation.

In some embodiments, at least one guide rail can be provided for hindering a test tube holder conveyed by the screw conveyor device from rotating with the helical track, so that the test tube holder contacting the helical track can be moved along the at least one guide rail while the helical track can be moved relative to the test tube holder by the rotating drive shaft. In one embodiment, a helical guide rail can be provided. The pitch angle of the guide rail can be considerably larger than that of the helical track, for example the pitch angle can be chosen so that the test tube holder can be rotated by about 180° about the helix axis upon the movement between the entry and the exit region. In some embodiments, at least one guide rail extending in parallel to the helix axis can be provided allowing for a simple design with low susceptibility to faults. In the case where the helical track is provided on the coaxial central shaft, in one embodiment, a tubular housing surrounding the helical track can be provided with guide rails. In the case where a rotating shaftless helical track is provided, guide rails can, in one embodiment, also be provided on the tubular housing surrounding the helical track. Alternatively or in addition, guide rails can be provided on the stationary central core element.

In alternative embodiments, in order to prevent a test tube holder conveyed by the screw conveyor device from rotating with the helical track, a second helical track having a parallel helix axis can be provided. In one embodiment, two co-rotating helical tracks of identical pitch can be provided. A test tube holder conveyed by the screw conveyor device can be guided between the two helical tracks. The device can also be referred to as twin screw conveyor device. Due to the co-rotating helical tracks contacting a test tube holder, forces acting in the two opposite tangential directions on the test tube holder can be balanced and the test tube holder can be reliably hindered from rotating with either one of the helical tracks.

In still another alternative embodiment, in the case where the helical track has a vertical helix axis, the helical track can be arranged fixed in position. The test tube holders can be slidingly moved along the helical track. For this purpose, in some embodiments, a rotary drum arranged coaxially to the helix axis and coupled to the drive shaft to rotate about the helix axis can be provided. The helical track can be arranged around or within the rotary drum. The rotary drum can be provided with at least one guide recess, in one embodiment, a plurality of guide recesses, adapted for receiving a test tube holder so that a test tube holder received in a guide recess can be moved upward or downward along the at least one guide recess while being moved along the helical track by the rotating rotary drum. Alternatively, a rotary tubular housing surrounding the helical track can be provided, which can be rotated about the helix axis and which can be provided with guiding elements for slidingly receiving test tube holders in parallel to the helix axis when moving the test tube holders along the helical track.

In one embodiment, a test tube holder conveyed by the at least one screw conveyor device can be slidingly moved relative to the helical track(s) along at least one of the leading surface of the helical track and the trailing surface of the helical track. In the context of the present disclosure, a leading surface of the helical track can be defined as the surface facing in the downstream direction of the movement path, and a trailing surface can be defined as the surface facing in the upstream direction of the movement path. For example, in the case where the test tube holders are moved upwards, the upward-facing surface can be referred to as the leading surface, whereas in the case where the test tube holders are moved downwards, the downward-facing surface can be referred to as the leading surface. As mentioned above, the helical track can be designed, for example, as a blade projecting from a central shaft or as a groove formed in the central shaft. The test tube holders, in one embodiment, can be provided with a rim engaging with the groove. In other embodiments, a body of the test tube holders can be arranged between the windings of one helical track contacting the leading surface and the trailing surface of adjacent windings of the helical track. In other embodiments, with vertical screw conveyor device having a helical track with a vertical helix axis, the test tube holder conveyed can be placed on the helical track so that its bottom surface can contacts the helical track. The distance between adjacent windings can be chosen sufficiently large to arrange test tube holders retaining test tubes between two windings. The surfaces contacting the test tube holders in some embodiments can be sufficiently smooth for allowing a relative motion between the helical track and the test tube holder with low friction.

A laboratory distribution system comprising at least one screw conveyer device with a helical track having a helix axis and a drive shaft having an axis of rotation parallel or coaxial to the helix axis can be provided. The drive shaft can be adapted to be driven to rotate about the axis of rotation for causing a movement of at least one test tube holder contacting the helical track between an entry region and an exit region. The entry region and the exit region can be spaced in a direction of the helix axis. Generally, each screw conveyor device can be operated in two directions by altering the direction of rotation of the drive shaft. In one embodiment, in use, each screw conveyor device can be operated only with one dedicated direction of rotation.

The at least one screw conveyor device can be a vertical screw conveyor device or a horizontal screw conveyor device.

In some embodiments, the laboratory distribution system can comprise at least a first vertical screw conveyer device for an upward movement of one test tube holder, or a plurality of test tube holders, and a second vertical screw conveyor device for a downward movement of one test tube holder, or a plurality of test tube holders. In each screw conveyor device, either empty test tube holders or test tube holders retaining test tubes or a combination of both can be transported between different levels.

In some embodiments, horizontal conveyor devices can be arranged between the first and the second vertical screw conveyor device. The horizontal conveyor devices can be independent from the vertical conveyor devices and any type of conveyor device may be provided between the first and the second vertical screw conveyor device. In one embodiment, at least one horizontal screw conveyor device can be provided between the first vertical screw conveyer device and the second vertical screw conveyer device.

In one embodiment, the screw conveyor device can be loaded or unloaded manually. In some embodiments, a loading module can be assigned to the at least one screw conveyor device. The loading module can be selected from a group comprising a ramp device, an accumulation pressure device, wherein test tube holders can be pushed into the screw conveyor device by subsequent test tube holders, a pusher, a screw conveyor device and a rotating collector device.

Alternatively or in addition, an unloading module can be assigned to the at least one screw conveyor device. The unloading module can be selected from a group comprising a rotating discharge device, a ramp and a belt drive device.

A laboratory automation system with a number of pre-analytical, analytical and/or post-analytical stations and with a laboratory distribution system can be provided. The laboratory distribution system can comprise at least one screw conveyer device with a helical track having a helix axis and a drive shaft having an axis of rotation parallel or coaxial to the helix axis. The drive shaft can be adapted to be driven to rotate about the axis of rotation for causing a movement of one test tube holder, or a plurality of test tube holders, contacting the helical track between an entry region and an exit region. The entry region and the exit region can be spaced in a direction of the helix axis.

A method can be made of a screw conveyor device in a laboratory distribution system for conveying test tube holders. The screw conveyor device can comprise a helical track having a helix axis and a drive shaft having an axis of rotation parallel or coaxial to the helix axis. The drive shaft can be driven to rotate about the axis of rotation for causing a movement of one test tube holder, or a plurality of test tube holders, contacting the helical track between an entry region and an exit region. The entry region and the exit region can be spaced in a direction of the helix axis.

FIGS. 1 to 5 show a first embodiment of a laboratory distribution system 1 comprising a first vertical screw conveyer device 2 for an upward movement of test tube holders 3, a second vertical screw conveyor device 4 for a downward movement of test tube holders 3 and a horizontal screw conveyor device 5. The first and second vertical screw conveyer device 2, 4 and the horizontal screw conveyor device 5 may be used in a configuration as shown in FIG. 1, for example, to buffer test tube holders 3 and/or to provide walkways or passageways. In other embodiments, at least one station of a laboratory automation system (not shown) can be arranged between the screw conveyer devices 2, 4, 5. In the figures, test tubes 30 can be retained in the test tube holders 3. In other embodiments, empty test tube holders 3 can be conveyed, or both empty and loaded test tube holders 3 can be conveyed.

The screw conveyor devices 2, 4, 5 each can comprise a helical track 20, 40, 50 having a helix axis 21, 41, 51 and a drive shaft 22, 42, 53 having an axis of rotation coaxial to the helix axis 21, 41, 51. Each drive shaft 22, 42, 52 can be driven to rotate about its axis of rotation, i.e. the respective helix axis 21, 41, 51 in the embodiment shown. In one embodiment, one common motor drive (not shown) can be provided. The drive shafts 22, 42, 52 can be coupled, for example by a gearing system to the one common motor drive. In other embodiments, each drive shaft 22, 42, 52 can be driven independently by designated a motor drive allowing the devices to convey the test tube holders 3 at differing speeds.

Each screw conveyor device 2, 4, 5 can be provided with a tubular housing 23, 43, 53 surrounding the helical track 20, 40, 50. The tubular housings 23, 43, 53 can be provided with grooves 230, 430, 530 allowing access to the test tube holders 3 inside the housing 23, 43, 53 in case of disturbances and/or an optical supervision of the system provided with non-transparent housings 23, 43, 53. The tubular housings 23, 43, 53 can each be provided with guide rails 24, 44, 54 extending in parallel to the respective helix axis 21, 41, 51.

Each vertical screw conveyor device 2, 4 can comprise a central shaft 25, 45 arranged coaxially to the drive shafts 22, 42 and coupled to the drive shafts 22, 42 to rotate with the drive shaft 22, 42, about the helix axis 21, 41. The helical tracks 20, 40 can be provided on the circumference of the respective central shaft 25, 45. Hence, when driving the drive shafts 20, 40, the helical tracks 20, 40 can be rotated about the helix axis 21, 41.

Each screw conveyor devices 2, 4, 5 can have an entry region 26, 46, 56 and an exit region 27, 47, 57, which can be spaced in a direction of the respective helix axis 21, 41, 51. In the embodiment shown, the exit region 27 of the first vertical screw conveyor device 2 can coincide with the entry region 56 of the horizontal screw conveyor device 5 and the exit region 57 of the horizontal screw conveyor device 5 can coincide with the entry region 46 of the second vertical screw conveyer device 5.

Figure 2:
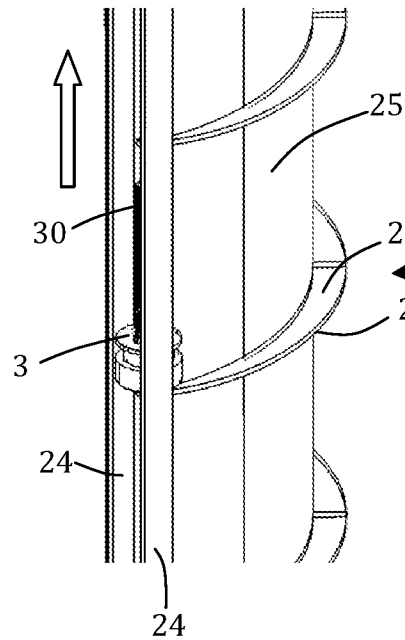
FIG. 2 illustrates a simplified detail II of the laboratory distribution system shown in FIG. 1 according to an embodiment of the present disclosure.

As best seen in FIGS. 2 and 5, in accordance with the first embodiment, the test tube holders 3 can be loaded to the helical tracks 20, 40 of the vertical screw conveyor devices 2, 4, in such a manner, that bottom surfaces of the test tube holders 3 can contact the helical tracks 20, 40. A movement of the test tube holders 3 in a radial direction of the central shafts 25, 45 can be confined by the central shafts 25, 45 and the tubular housings 23, 43. For a better visualization, the housing 23 is not shown in FIG. 2. The test tube holders 3 can abut in the circumferential direction of the central shafts 25, 45 the guide rails 24, 44. The guide rails 24, 44 can hinder the test tube holders 3 from moving with the helical tracks 20, 40 along the circumferential direction of the central shafts 25, 45.

Hence, driving the drive shafts 22, 42 to rotate about the helix axis 21, 41 can cause the test tube holders 3 loaded to the helical track 20, 40 to move in a vertical direction along the guide rails 24, 44 between the entry region 26, 46 and the exit region 27, 47.

As best seen in FIG. 2, in this embodiment, the test tube holders 3 conveyed by the first vertical screw conveyor device 2 can be slidingly moved relative to the helical track 20 along the leading surface 200 of the helical track 20. In the context of the present disclosure, the leading surface 200 of the helical track 20 can be defined as the surface facing in the downstream direction of the movement path indicated by an arrow, i.e., as the test tube holders 3 are moved upwards conveyed by the first vertical screw conveyor device 2, the upward-facing surface can be referred to as the leading surface 200. The opposite surface facing in the upstream direction of the movement path can be referred to as trailing surface 201.

As best seen in FIG. 5, in this embodiment, the test tube holders 3 conveyed by the second vertical screw conveyor device 4 can be slidingly moved relative to the helical track 40 along the trailing surface 401 of the helical track 40, i.e. the surface facing in the upstream direction of the movement path indicated by an arrow. In other words, as the test tube holders 3 are moved downwards, the upward-facing surface can be referred to as the trailing surface 401 of the second vertical screw conveyor device 4.

The test tube holders 3 can be provided with a groove. In other embodiments, the groove can engage with the helical track 20, 40.

Figure 3:
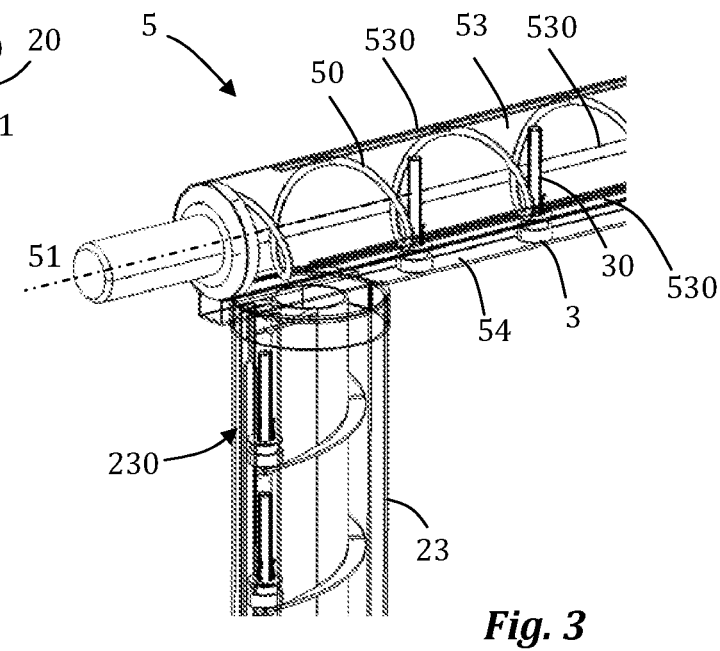
FIG. 3 illustrates a detail III of the laboratory distribution system shown in FIG. 1 according to an embodiment of the present disclosure.

As shown in FIG. 3, for the horizontal screw conveyor device 5, a shaftless helical track 50 can be provided, which can be coupled at one end to the drive shaft 52, allowing the test tube holders 3 with test tubes 30 retained therein to extend between the windings of the helical track 50 without any interference.

As shown in FIG. 4, in accordance with the first embodiment, at the entry region 26, the first vertical screw conveyor device 2 can be loaded automatically. A rotating collector device can be provided as a loading module 28, which can be coupled to the central shaft 25 to rotate with the central shaft 25. The rotating collector device provided as the loading module 28 can comprise a collector arm 280 for pushing a test tube holder 3 onto the helical track.

Similar as shown in FIG. 5, the screw conveyor devices 2, 4, 5 can be unloaded automatically. In the first embodiment at the exit region 47 of the second vertical screw conveyor device, a rotating discharge device can be provided as the unloading module 49, which can have a cam 491 for pushing the test tube holders 3 of the helical track 40 and onto a horizontal conveyor device 6 such as, for example, a belt drive device or a guide rail.

As shown by broken lines in FIG. 1, in one embodiment, one or more of the screw conveyor devices 2, 4, 5 can be provided with an additional entry region 8, or an additional exit region, for feeding additional test tube holders 3 or removing test tube holders at different stations of the system. The additional entry or exit regions, in one embodiment, can be offset in circumferential direction to the first entry or exit region. In the embodiment shown, the additional entry region 8 can be offset by about 180°. In other embodiments, the entry region can be offset by, for example, about 90°. Of course, provision can be made to avoid a collision of the test tube holders 3 and to allow a transfer of all test tube holders to the downstream conveyor and/or station.

In still a further embodiment, at least one additional entry region, or one additional exit region, of one screw conveyor device 2, 4, 5 can be aligned to the entry region 26, 46, 56 and the exit region 27, 47, 57 to allow the use of the respective guide rails 24, 44, 54. This embodiment can be used as a lift connecting several different levels distributed along the axis 21, 41, 51. For complete lift functionality, at least two parallel screw conveyors may be necessary, one for upstream motion and one for downstream motion.

FIG. 6 shows an alternative embodiment of a loading module 28 for the first vertical screw conveyer device of a laboratory distribution system similar to that shown in FIGS. 1 to 5. In the embodiment shown in FIG. 6, the loading module 28 can be a screw conveyor device comprising a helical track 281. The test tube holders 3 can be positioned between two adjacent windings of the helical track 281 for transporting the test tube holders towards a vertical screw conveyor device 2 (not shown in FIG. 6).

FIGS. 7 to 10 show a third embodiment of a laboratory distribution system 1 comprising a first vertical screw conveyer device 2 for an upward movement of test tube holders 3, a second vertical screw conveyor device 4 for a downward movement of test tube holders 3 and a horizontal screw conveyor device 5 similar to that shown in FIGS. 1 to 5. In contrast to the embodiment shown in FIGS. 1 to 5, each screw conveyor device 2, 4, 5 can comprise two co-rotating helical tracks 20, 120; 40, 140; 50, 150 of identical pitch. Each helical tracks 20, 120; 40, 140; 50, 150 can be driven by a drive shaft to rotate about the respective helix axis 21, 121, 41, 141, 51, 151. Either one common drive shaft for the two helical tracks 20, 120; 40, 140; 50, 150 of one screw conveyor device 2, 4, 5 or two synchronized drive shafts can be provided.

Figure 10:
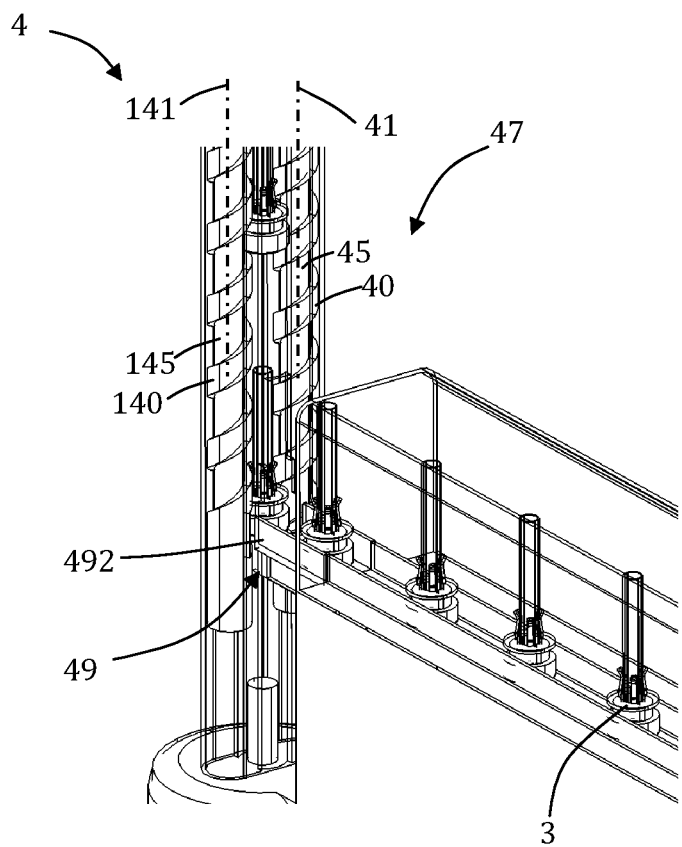
FIG. 10 illustrates a detail IX of a laboratory distribution system shown in FIG. 7 similar to FIG. 3 according to an embodiment of the present disclosure.

Test tube holders 3 conveyed by the screw conveyor device can be guided between the two helical tracks 20, 120; 40, 140; 50, 150 as shown in FIGS. 8 to 10. In the embodiment shown, each helical track 20, 120; 40, 140; 50, 150 can have a pitch that can be adapted to the size of a body of the test tube holder 3 such that the test tube holders 3 can be arranged between the adjacent windings of the helical tracks 20, 120; 40, 140; 50, 150. At the exit region 47 of the second vertical screw conveyor device 4 as shown in FIG. 10, an unloading module 49 comprising a ramp 492 can be provided. In an alternative embodiment, a band drive can be provided as unloading module or downstream of the unloading module.

Figure 11:
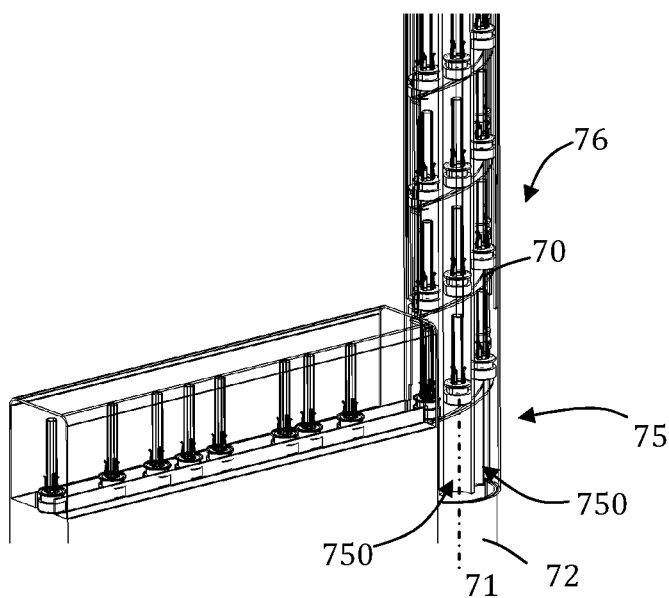
FIG. 11 illustrates an entry region of a vertical screw conveyer according to an embodiment of the present disclosure.

FIG. 11 shows an entry region 76 of an alternative embodiment of a vertical screw conveyer device 7 comprising a helical track 70 having a helix axis 71 and a drive shaft 72 having an axis of rotation coaxial to the helix axis 71. In accordance with the embodiment shown in FIG. 11, a drum 75 can be provided coaxially arranged to the helical track 70.

Figure 12:
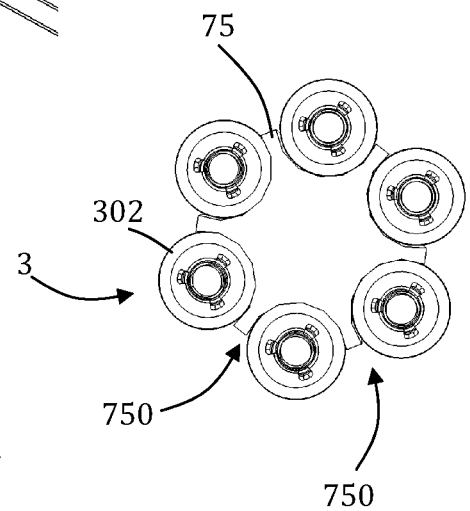
FIG. 12 illustrates top view of a drum of the vertical screw conveyer of FIG. 11 according to an embodiment of the present disclosure.

FIG. 12 is a schematic top view of the drum 75. As shown in FIGS. 11 and 12, the drum 75 can be provided with a plurality of guide recesses 750 extending in parallel to the helix axis 71, which can be adapted for receiving a test tube holder 3. In the embodiment shown, six guide recesses 750 can be provided evenly distributed about the circumference of the drum 75. The size of the drum 75 and the guide recesses 750 can be adapted to the size of the test tube holders 3 such that the guide grooves 750 can be semicircular with a radius corresponding to that of a body 302 of the test tube holders 3 and the center axis of the test tube holders 3 guided in the guide grooves 750 can be at least approximately arranged on the shell surface of the drum 75.

In accordance with the embodiment shown in FIG. 11, the helical track 70 can be arranged fixed in position around the coaxial drum 75 and the drum 75 can be coupled to the drive shaft 72 to rotate about the helix axis 71. In an alternative embodiment, the drum 75 can be arranged fixed in position. The helical track 70 can be arranged on a housing surrounding the drum 75 and driven by the drive shaft 72 to rotate about the drum 75.

In each case, driving the drive shaft 72 can cause the drum 75 to rotate about the helix axis 71 in relation to the helical track 70 and the test tube holders 3 received in the guide recesses 750 can be moved upward along the guide recesses 750 while being pushed along the helical track 70 by the drum 75. As shown in FIG. 11, such a device can be advantageous for buffering a plurality of test tube holders 3.

In a variant of the embodiments described in the context of FIG. 12, the screw conveyor device 7 can comprise a plurality of entry and exit regions. This can be advantageous for example for providing a storage unit having several levels.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A conveyor device for conveying test tube holders in a laboratory distribution system, the conveyor device comprising:
    a screw conveyor device comprising,
        a helical track having a helix axis, and
        a drive shaft having an axis of rotation parallel, or coaxial, to the helix axis, wherein the drive shaft is adapted to be driven to rotate about the axis of rotation for causing a movement of a test tube holder or a plurality of test tube holders contacting the helical track between an entry region and an exit region, wherein the test tube holder or the plurality of test tube holders move in parallel to the helix axis, wherein the entry region and the exit region are spaced in a direction of the helix axis, and wherein the screw conveyor device is a vertical screw conveyor device having a vertical helix axis.

2. The conveyor device according to claim 1, wherein a test tube holder conveyed by the screw conveyor device is slidingly moved relative to the helical track(s) along at least one of the leading surface of the helical track and the trailing surface of the helical track.

3. The conveyor device according to claim 1, wherein the helical track is coupled to the drive shaft to rotate about the helix axis.

4. The conveyor device according to claim 3, wherein the helical track is provided on a coaxial central shaft.

5. The conveyor device according to claim 4, wherein at least one guide rail is provided for hindering a test tube holder conveyed by the screw conveyor device from rotating with the helical track, so that a test tube holder contacting the helical track is moved along the at least one guide rail while the helical track is moved relative to the test tube holder by the rotating drive shaft.

6. The conveyor device according to claim 5, wherein the at least one guide rail extending in parallel to the helix axis.

7. The conveyor device according to claim 4, wherein two co-rotating helical tracks of identical pitch are provided, wherein a test tube holder conveyed by the screw conveyor device is guided between the two helical tracks.

8. A laboratory distribution system comprising at least one screw conveyer device, the screw conveyer device comprising:
    a helical track having a helix axis, and
    a drive shaft having an axis of rotation parallel, or coaxial, to the helix axis, wherein the drive shaft is adapted to be driven to rotate about the axis of rotation for causing a movement of a test tube holder or a plurality of test tube holders contacting the helical track between an entry region and an exit region, wherein the test tube holder or the plurality of test tube holders move in parallel to the helix axis, wherein the entry region and the exit region are spaced in a direction of the helix axis, and wherein the screw conveyor device is a vertical screw conveyor device having a vertical helix axis.

9. The laboratory distribution system according to claim 8, wherein a loading module is assigned to the at least one screw conveyor device.

10. The laboratory distribution system according to claim 9, wherein the loading module is selected from a group comprising a ramp device, an accumulation pressure device, a pusher, a screw conveyor device and a rotating collector device.

11. The laboratory distribution system according to claim 8, wherein a first vertical screw conveyer device for an upward movement of one test tube holder, or a plurality of test tube holders, and a second vertical screw conveyor device for a downward movement of one test tube holder, or a plurality of test tube holders, is provided.

12. The laboratory distribution system according to claim 11, wherein at least one horizontal screw conveyor device is provided between the first vertical screw conveyer device and the second vertical screw conveyor device.

13. The laboratory distribution system according to claim 11, wherein an unloading module is assigned to the at least one screw conveyor device.

14. The laboratory distribution system according to claim 13, wherein the unloading module in is selected from a group comprising a rotating discharge device, a ramp and a belt drive device.

15. A method of using a screw conveyor device in a laboratory distribution system for conveying test tube holders, the screw conveyor device comprising a helical track having a helix axis and a drive shaft having an axis of rotation parallel, or coaxial, to the helix axis, wherein the screw conveyor device is a vertical screw conveyor device having a vertical helix axis, the method comprising:
- driving the drive shaft to rotate about the axis of rotation resulting in a movement of one test tube holder, or a plurality of test tube holders;
- moving the test tube holder or the plurality of test tube holders in parallel to the helix axis; and
- contacting the helical track between an entry region and an exit region, wherein the entry region and the exit region are spaced in a direction of the helix axis.

* * * * *